(12) United States Patent
Jongen et al.

(10) Patent No.: US 8,481,951 B2
(45) Date of Patent: Jul. 9, 2013

(54) DEVICE AND METHOD FOR PARTICLE THERAPY VERIFICATION

(75) Inventors: Yves Jongen, Louvain-la-Neuve (BE); Frédéric Stichelbaut, Mazy (BE)

(73) Assignee: Ion Beam Applications S.A., Louvain-la-Neuve (BE)

( * ) Notice: Subject to any disclaimer, the term of this patent is extended or adjusted under 35 U.S.C. 154(b) by 0 days.

(21) Appl. No.: 13/002,484

(22) PCT Filed: Jul. 3, 2009

(86) PCT No.: PCT/EP2009/058458
§ 371 (c)(1), (2), (4) Date: Mar. 30, 2011

(87) PCT Pub. No.: WO2010/000857
PCT Pub. Date: Jan. 7, 2010

(65) Prior Publication Data
US 2011/0186720 A1  Aug. 4, 2011

(30) Foreign Application Priority Data
Jul. 3, 2008  (EP) .................................. 08159577

(51) Int. Cl.
*G21K 1/02* (2006.01)
(52) U.S. Cl.
USPC ............... 250/363.1; 250/363.05; 250/363.08
(58) Field of Classification Search
USPC .............................. 250/363.1, 363.05, 363.08
See application file for complete search history.

(56) References Cited

U.S. PATENT DOCUMENTS

| | | | |
|---|---|---|---|
| 3,011,057 A * | 11/1961 | Anger | 250/366 |
| 4,501,964 A | 2/1985 | Arnold | |
| 6,177,675 B1 | 1/2001 | Gagnon et al. | |
| 8,049,176 B1 * | 11/2011 | Majewski et al. | 250/363.1 |
| 8,357,907 B2 * | 1/2013 | Testa et al. | 250/370.07 |
| 2011/0284757 A1 * | 11/2011 | Butuceanu et al. | 250/389 |

FOREIGN PATENT DOCUMENTS

| | | |
|---|---|---|
| DE | 196 03 212 C1 | 5/1997 |
| WO | 01/79884 A3 | 10/2001 |

OTHER PUBLICATIONS

Testa et al., Real-time monitoring of the Bragg-peak position in ion therapy by means of single photon detection, 2010, Radiat Environ Biophys, p. 337-343.*
Frandes et al., A Tracking Compton-Scattering Imaging System for Hadron Therapy Monitoring, 2010, IEEE Transactions on Nuclear Science, vol. 57, pp. 144-150.*
Peterson et al., Optimizing a three-stage Compton camera for measuring prompt gamma rays emitted during proton radiotherapy, 2010, Phys. Med. Biol. vol. 55, pp. 6841-6856.*
Polf et al., Measurement and calculation of characteristic prompt gamma ray spectra emitted during proton irradiation, 2009, Phys. Med. Biol. vol. 54 , pp. N519-N527.*

(Continued)

*Primary Examiner* — Christine Sung
(74) *Attorney, Agent, or Firm* — Fitch, Even, Tabin & Flannery LLP

(57) ABSTRACT

The invention is related to the field of charged Hadron Therapy, i.e. radiation therapy using strongly interacting particles. More particularly, the invention relates to a detector and method for measuring the beam range of a charged hadron beam in a target object as well as the particle dose distribution in the target object.

32 Claims, 5 Drawing Sheets

OTHER PUBLICATIONS

Richard et al., Design Study of a Compton Camera for Prompt γ Imaging During Ion Beam Therapy, 2009, IEEE Nuclear Science Symposium Conference Record, pp. 4172-4175.*

Chul-Hee Min and Chan Hyeong Kim. "Prompt Gamma Measurements for Locating the Dose Falloff Region in the Proton Therapy." Applied Physics Letters, AIP, American Institute of Physics, Melville, NY, vol. 89, No. 18, Nov. 2, 2006, p. 183517-1-183517-3.

Chul Hee Min et al., "Development of an Array-Type Prompt Gamma Detection System for the Online Measurement of the Range of the Proton Beam in a Patient: a Monte Carlo Feasibility Study." Journal of the Korean Physical Society, vol. 52, No. 3, Mar. 15, 2008, pp. 888-891.

Daniela Möckel et al., "Comparison of In-Beam and Off-Beam PET Experiments at Hard Photons." IEEE Nuclear Science Symposium Conference Record, 2007, pp. 4113-4116.

International Patent Application No. PCT/EP2009/058458, International Search Report and Written Opinion of the International Searching Authority, date of actual completion of the international search Oct. 7, 2009, 9 pages (corresponds to U.S. Appl. No. 13/002,484).

* cited by examiner

1a

1b

1c

DEVICE AND METHOD FOR PARTICLE THERAPY VERIFICATION

CROSS REFERENCE To RELATED APPLICATIONS

This application is a national phase application of International Application No. PCT/EP2009/058458, filed Jul. 3, 2009, designating the United States and claiming priority to European Patent Application No. 08159577.9, filed Jul. 3, 2008, both of which are incorporated by reference herein in their entirety.

FIELD OF THE INVENTION

The invention is related to the field of charged Hadron Therapy, i.e. radiation therapy using strongly interacting particles. More particularly, the invention is related to a detector and method for measuring the beam range of a charged hadron beam in a target object as well as the particle dose distribution in the target object.

STATE OF THE ART

It is well established that charged hadrons (i.e., protons, pions, ions such as carbon ions) have physical advantages with respect to X-rays or gamma rays in the field of radiation therapy. For example, protons of a given energy (i.e. forming a mono-energetic proton beam), have a certain range or penetration depth in a target object and do not penetrate beyond that range, and furthermore, they deposit their maximum amount of energy or dose in the so-called Bragg Peak, which corresponds to the point of greatest penetration of the radiation in the target volume. Since the Bragg peak position depends on the energy of the hadron beam, it is evident that by precisely controlling and modifying the energy one can place the Bragg Peak at a suited depth of a tumour so as to administer the greatest radiation energy to selected points and spare, by contrast, healthy tissue surrounding said points.

As a consequence, the location of the Bragg peak must be precisely known since critical tissue localized near the target tumor could receive overdoses, whereas conversely the target tumor could receive underdoses.

Even if existing radiation treatment planning tools calculate a "theoretical" or "planned" beam range and dose distribution based on CT images, it is almost impossible to fully take into account the complex atomic composition of surrounding tissues. As a consequence, a degree of uncertainty is affecting the particle range. There is a need therefore to obtain a direct on-line, i.e. during beam delivery, measurement of the particle range.

The direct detection of the end of the dose deposition of a hadron beam is impossible since the hadron beam stops inside the treatment volume, even during the irradiation.

A solution could be the detection of secondary particles giving quantitative information on the dose deposition of the particle beam. Such a strategy was disclosed in document 'Comparison of In-Beam and Off-beam PET Experiments at Hard Photons', Möckel et al, 2007 IEEE Nuclear Science Symposium Conference Record, p. 4113-4116. This document describes the measurement of β+ activity distribution simultaneously—on-line—with the irradiation with a hard photon beam. In brief, positron emitters are generated in a phantom by hard photon irradiation (energy above ~20 MeV) due to (γ,n) reaction, leading to pair annihilation and subsequent emission of two coincident gammas. Möckel et al used a double head PET camera that moved linearly in the beam direction to detect these gammas and deduced a two-dimensional activity distribution.

For proton beams this principle can not be used due to differences in the mechanisms for producing PET isotopes with proton beams when compared with carbon beams. Indeed the distribution in the target object of positron emitters produced by proton-induced nuclear reactions is not directly correlated with the spatial proton dose distribution in the target object. Moreover the cross sections for producing positron emitter PET isotopes with proton beams are much smaller when compared with the cross sections for producing the PET isotopes with carbon beams. As positron emitters generated by the particle beam—mainly $^{11}C$ and $^{15}O$—have different half-life the delay between irradiation and the off-beam PET scanning can affect the determination of the dose deposition. Moreover, the leakage of positron emitters to the blood flow will also affect the dose deposition measurement by off-beam PET scanning.

Another solution is disclosed in the document 'Prompt gamma measurements for locating the dose falloff region in the proton therapy', Chul-Hee Min and Chan Hyeong Kim, 2006 Applied Physics Letters, article 183517. Chul-Hee and Chan Hyeong Kim used a gamma scintillation camera equipped with one multilayered collimator system to measure prompt gamma generated by irradiation. Nevertheless, this device is only able to detect prompt gamma emitted from 90° of the beam direction. To obtain the prompt gamma distribution along the beam direction, the detector needs to be moved step by step to different measurement positions which makes this device not useful for practical on-line measurements.

Chul-Hee Min et al in Journal of the Korean Physical Society, Vol 52, N° 3, March 2008, pp 888-891 disclosed a linear array of scintillation detectors and photodiodes for the online measurement of the proton beam range. One of the disadvantages of this device is the increased level of background as result of reduced collimator shielding.

AIMS OF THE INVENTION

It is an object of the present invention to provide a device and a method for charged hadron therapy verification which overcomes the drawbacks of prior art detectors and methods. More particularly, it is an object of the present invention to provide an on-line detector, i.e. a detector which is capable of providing real-time measurements of the penetration depth or range of the charged hadron beam in an object or in a body irradiated by the charged hadron beam. Moreover, the spatial dose distribution in an object or in a body irradiated by a charged hadron beam can be determined.

SUMMARY OF THE INVENTION

The present invention relates to a device for charged hadron therapy verification by detecting prompt gammas produced when irradiating an object or a body with a charged hadron beam, said device comprising a gamma-ray pin-hole camera arranged to acquire the number of said prompt gammas emitted while the said charged hadron beam is penetrating the said object or body.

Preferably, the gamma-ray pin-hole camera comprises shielding means to avoid detection of unwanted particles.

Preferably, the gamma-ray pin-hole camera comprises electronic means for data acquisition.

Preferably, the device according to the present invention further comprises computing means connected to said electronic means enable to determine from the counted said prompt gammas a measured penetration depth or range of said charged hadron beam in said object or body.

Preferably, said computing means enable to compare the said measured penetration depth with the theoretical or planned penetration depth.

Preferably, said computing means connected to said electronic means enable to build an image representing the relative dose deposition.

Preferably, said image is a two-dimensional or three-dimensional representation of the relative dose deposition.

Preferably, the optical axis of the camera is perpendicular to the direction of the beam.

Preferably, the inner diameter d of the pinhole is strictly superior to the value of the wavelength of the most energetic emitted prompt gammas.

Preferably, the device according to the present invention further comprises electronic means to acquire the said number of said prompt gammas in synchrony with the time structure of said charged hadron beam.

Preferably, the device according to the present invention comprises at least two camera for detecting prompt gammas.

Another aspect of the present invention relates to a method for charged hadron therapy verification by detecting prompt gammas obtained by irradiating a phantom with a particle beam comprising the steps of:
  irradiating the phantom with a charged hadron beam;
  detecting the emitted prompt gammas during irradiation;
  deducing from the detected prompt gammas the range or penetration depth of the said charged hadron beam;
  measuring the range of the charged hadron beam in the phantom with a dedicated range measuring device;
  comparing the deduced range based on the prompt gamma detection with the range measured with the said dedicated range measuring device.

Preferably, the method according to the present invention further comprises the step of:
  calculating the radiation dose given to the phantom based on the said detected prompt gammas.

Preferably, the method according to the present invention further comprises before the irradiation step the step of:
  positioning a prompt gamma detector in a fixed position relatively to the phantom.

Preferably, the prompt gamma detector used in the method according to the present invention is a gamma-ray pinhole camera.

The present invention also relates to a hadron therapy device for charged hadron range verification by detecting and/or quantifying prompt gammas produced when irradiating an object or a body with a charged hadron beam, said device comprising a gamma-ray pin-hole camera arranged to acquire the number of said prompt gammas emitted while the said charged hadron beam is penetrating the said object or body.

Preferably, said gamma-ray pin-hole camera comprises shielding means to avoid detection of particles different from prompt gammas.

Preferably said gamma-ray pin-hole camera comprises electronic means for data acquisition.

Preferably the hadron therapy device further comprises computing unit, connected to said electronic means, for determining—from the counted said prompt gammas—a measured penetration depth or range of said charged hadron beam in said object or body.

Preferably said computing unit compares the said measured penetration depth with the theoretical or planned penetration depth.

Preferably said computing unit, connected to said electronic means, builds an image representing the relative dose deposition.

Preferably said image is a two-dimensional or three-dimensional representation of the relative dose deposition.

Preferably the optical axis of the camera is perpendicular to the direction of the beam.

Preferably the inner diameter d of the pinhole is strictly superior to the value of the wavelength of the most energetic emitted prompt gammas.

Preferably the hadron therapy device further comprises electronic means to acquire the said number of said prompt gammas in synchrony with the time structure of said charged hadron beam.

Another aspect of the present invention relates to a method for charged hadron range verification by detecting prompt gammas comprising the steps of:
  irradiating with a charged hadron beam;
  detecting the emitted prompt gammas;
  deducing from the detected prompt gammas the range or penetration depth of the said charged hadron beam;
  measuring the range of the charged hadron beam with a dedicated range measuring device;
  comparing the deduced range based on the prompt gamma detection with the range measured with the said dedicated range measuring device.

The method according to the present invention further comprises the step of:
  calculating the radiation dose based on the said detected prompt gammas.

The method according to the present invention further comprises before the irradiation step the step of:
  positioning a prompt gamma detector in a fixed position relatively to the treatment room.

Preferably the prompt gamma detector used in the method is a gamma-ray pin-hole camera.

DETAILED DESCRIPTION OF THE INVENTION

The present invention relates to a device for charged hadron therapy verification by detecting prompt gammas when irradiating an object or a body with a charged hadron beam (e.g. proton beam, carbon beam), said device comprising counting means arranged to acquire the number of said prompt gammas emitted while the said charged hadron beam is penetrating the said object or body Preferably, said counting means comprise a camera comprising a plurality of collimators coupled to at least one scintillation crystal, said crystal being coupled to photomultiplier tubes and electronic means for data acquisition.

More preferably, said counting means comprise a gamma-ray pin-hole camera comprising electronic means for data acquisition.

Preferably, said counting means comprise shielding means to avoid detection of unwanted particles.

Preferably, computing means connected to said electronic means enable to determine from the counted said prompt gammas a measured penetration depth or range of said charged hadron beam in said object or body.

Furthermore, computing means enable to compare the said measured penetration depth with the theoretical or planned penetration depth.

Preferably computing means connected to electronic means enable to build an image representing the relative dose deposition.

Preferably said image is a two-dimensional or three-dimensional representation of the relative dose deposition.

Preferably the optical axis of the camera is perpendicular to the direction of the beam.

Moreover, the present invention relates to a method for charged hadron therapy verification by detecting prompt gammas obtained by irradiating a phantom with a particle beam comprising the steps of irradiating of a phantom with a charged hadron beam, detecting the emitted prompt gamma during irradiation, deducing from the detected prompt gammas the range or penetration depth of the said charged hadron beam, measuring the range of the charged hadron beam in the phantom with a dedicated range measuring device and comparing the deduced range based on the prompt gamma detection with the range measured with the said dedicated range measuring device.

In addition, the dose delivered to the object can be calculated based on the measured prompt gammas.

The present invention is based on the detection of prompt gamma obtained by irradiation of human body, animal body or any object such as a water phantom.

Figure 1:
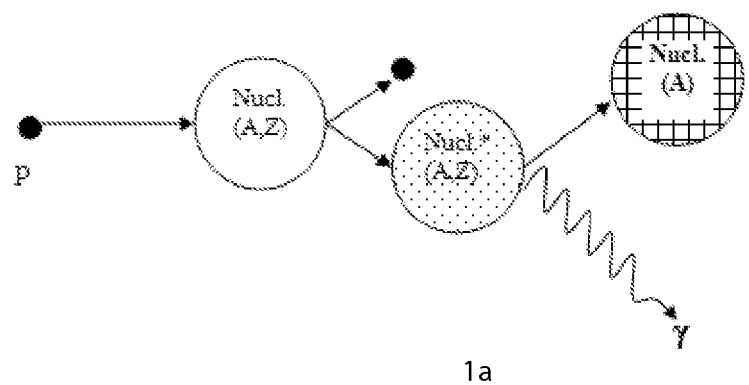
FIG. 1a presents an example of a nuclear reaction that can occur in a body or an object irradiated with a proton beam.
FIG. 1b presents another example of a nuclear reaction that can occur in a body or in an object irradiated with a proton beam.
FIG. 1c presents yet another example of a nuclear reaction that can occur in a body or in an object irradiated with a proton beam.
Figure 1:
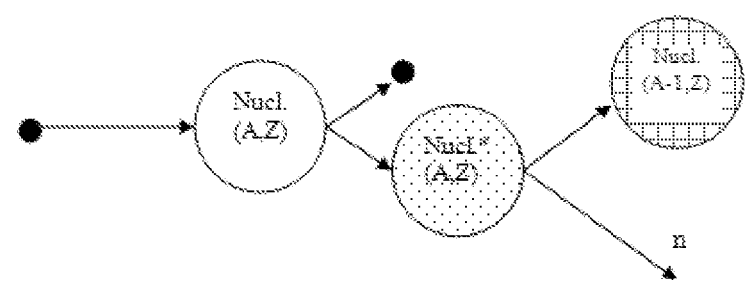
Figure 1:
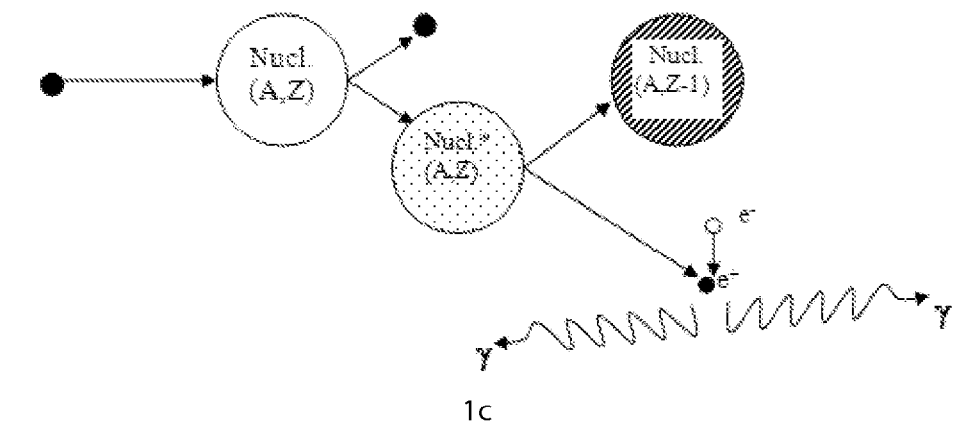

Following irradiation with a charged hadron beam, such as a proton beam, a nucleus in an excited state can return to his ground state thanks to several nuclear reactions, several of them being depicted in FIG. 1. Among these reactions the emission of a prompt gamma can be observed directly after interaction with a proton from the beam, as shown in FIG. 1a.

The correlation between the energy deposition of charged hadron beams and the distribution of prompt gammas was theorically assessed by Monte Carlo simulation using both PHITS (Proton and Heavy Ion Transport System) and MCNPX 2.5.0 (Monte Carlo N-Particle eXtended version 2.5.0) codes.

Figure 2:
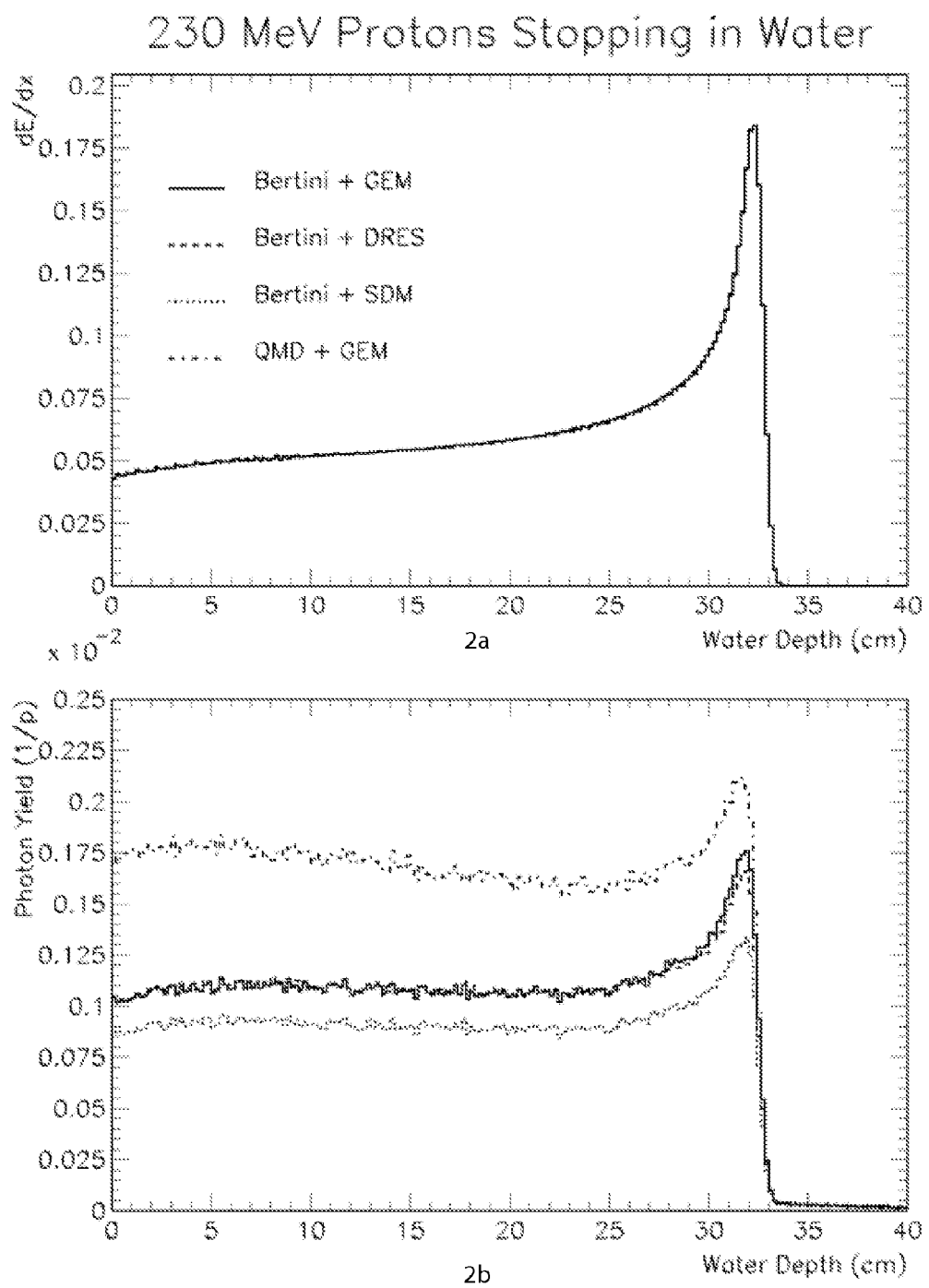
FIG. 2a presents Monte Carlo simulations of the energy loss or dose deposition of a 230 MeV proton beam as function of the penetration depth in water, comparing different Monte Carlo codes.
FIG. 2b presents Monte Carlo simulations of relative prompt gamma production vertex along proton beam path (i.e. photon yield per proton), comparing different Monte Carlo codes.

Monte Carlo simulation results for a 230 MeV monoenergetic proton beam—irradiating a water phantom—are displayed at FIG. 2.

The depth-dose distribution (FIG. 2a) displays the relative energy deposition or dose deposition in the water phantom as function of the penetration depth of the hadron beam in the water phantom.

A maximum in the dose distribution, the so-called Bragg peak, is observed at a depth of about 32 cm in the water phantom.

The 90% value of the dose distribution at the right side of the Bragg peak is called the penetration depth or range of the hadron beam in the object (e.g. water phantom, body).

Other definitions of the range of the hadron beam exist (eg 80% value, . . . ).

The depth-dose distribution of the proton beam (FIG. 2a) is tightly correlated to the prompt gamma yield (FIG. 2b).

The prompt gamma yield (FIG. 2b) displays the relative number of prompt gammas emitted as function of the charged hadron penetration depth in the water phantom.

A peak in the prompt gamma spectrum (FIG. 2b) is observed at about the same depth position as the Bragg peak position in the depth-dose distribution spectrum (FIG. 2a).

The water phantom considered in these simulations is a 40 cm long cylinder with 20 cm diameter.

Beside the emission of prompt gamma, other particles are emitted while irradiating human body, animal body or any object. In particular, as shown in FIG. 1b, fast neutrons are produced and constitute the major source of background affecting the prompt gamma counting signal.

Figure 3:
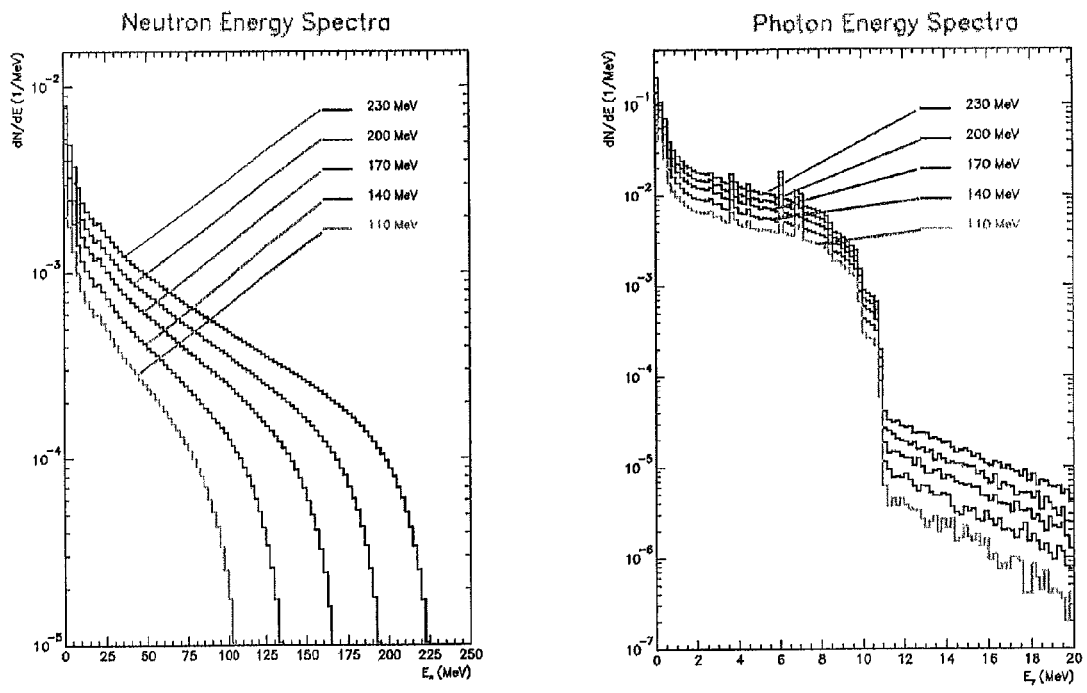
FIG. 3a presents Monte Carlo simulations of neutron spectra resulting from irradiating a body or an object with proton beams of various energies.
FIG. 3b presents Monte Carlo simulations of photon spectra resulting from irradiating a body or an object with proton beams of various energies.

Simulated spectra of fast neutrons—for different proton beam energies—are displayed at FIG. 3, PHITS code being used for Monte Carlo simulation.

Although fast neutrons are mainly forward oriented, they largely contribute to the deterioration of the signal after being scattered on the wall of the treatment room. An appropriate shielding of the detector is therefore required against neutrons.

Shielding against other particles such as X-ray generated by bremmstrahlung is also required.

Preferably, the device according to the present invention comprises at least two camera for detecting prompt gammas.

Said cameras can either by identical or different.

Preferably the prompt gammas counting occurs in synchrony with the time structure of the particle beam provided by the accelerator.

In the present invention, the term "time structure" refers to the variation of the beam intensity as function of time.

In most cases, said beam intensity varies in time and depends on the characteristics of the particle accelerator.

Two examples of time structures will be described hereafter for two types of particle accelerators suitable for particle therapy.

The time structure of a particle accelerator (e.g. cyclotron, synchrocyclotron, linear accelerator, . . . ) is determined by the Radiofrequency (RF) accelerator system.

For example a 230 MeV proton cyclotron using a constant RF frequency of 100 MHz will deliver a beam pulse every 10 nsec (=beam pulse repetition period) and have a pulse width of typically 1 nsec.

Another example of a particle accelerator is a 250 MeV synchrocyclotron using a time varying RF frequency whereby the frequency changes from high to low in order to take into account the effect of the relativistic mass increase of the particle. During the acceleration cycle of a particle in the synchrocyclotron, the RF frequency can for example vary between 86 MHz and 66 MHz. This acceleration cycle is then repeated for each beam pulse to be produced.

The typical repetition frequency of the acceleration cycle (corresponding to the RF modulation frequency) is between 200 and 1000 Hz. As a result, the time structure of a particle beam produced with a synchrocyclotron has a macro-level and a micro-level time structure.

The macro-level time structure corresponds to a macro-level pulse produced every acceleration cycle e.g. every 2 ms (i.e. for a RF modulation frequency of 500 Hz) and has a typical width of a few hundred nanoseconds (e.g. 0.3 microseconds).

This macro-level pulse comprises a series of micro-level pulses where the frequency of the micro-level pulses corresponds to the RF acceleration frequency.

For an RF frequency of 66 MHz, this means that a micro-level pulse is produced every 15.2 nanoseconds with a pulse width of typically 1.5 nanoseconds.

For example, a macro-level pulse can comprise a series of 20 micro-level pulses.

To improve the ratio between the prompt gammas and the background radiation one can advantageously make use of the time structure of a particle accelerator as described above.

After interaction of the particle beam with a target (human body, animal body or any object such as a water phantom), the time it takes before a radiation event is detected by a said gamma camera will depend on the type of radiation event.

The prompt gammas, travelling at the speed of light, will promptly generate a radiation invent in the gamma camera while the slower neutrons will generate a radiation event in the gamma camera at a later time.

After production of prompt gammas (following the interaction of the particle beam with the target), the time window during which prompt gammas can be detected in the gamma camera is small (for example of the order of a few nanoseconds or less).

The neutrons not only interact at a later moment in time with the gamma camera when compared to the fast prompt gammas but the time window during which neutrons (having a broad energy spectrum) can be detected in the gamma camera, after the beam has hit the target, is much larger and can be several tens of nanoseconds and more (depending on the target to gamma camera geometry).

It is this difference in time of flight (TOF) between the prompt gammas and neutrons before they generate a radiation event in the gamma camera that can be used to enhance the prompt gamma signal intensity with respect to the background radiation intensity (neutrons and neutron induced radiation).

The time structure of the particle accelerators discussed above producing for example pulses every 10 ns and having a pulse width of 1 ns are well suited to optimize the signal to background ratio of the prompt gammas detected with a gamma camera.

By measuring the prompt gammas in synchrony with the RF accelerator frequency of the particle accelerator, prompt gammas only need to be acquired during a small time window after the beam has hit the target and prompt gammas were produced.

The amount of background reduction will depend on the time window selected for analysing the prompt gammas with respect to the beam pulse repetition period.

In the case of a cyclotron as mentioned above where the beam pulse repetition period is 10 nanoseconds and the pulse width is 1 nanosecond, the background radiation can be reduced by a maximum factor of 10 when applying for example a prompt gamma time window of 1 ns.

For the case of a synchrocyclotron where for example 20 beam pulses having a duration of 1.5 nanoseconds are delivered for each acceleration cycle period of 2 milliseconds, the background level can be reduced by a maximum factor of 66666 when setting for example the prompt gamma window to 1.5 ns.

Preferably the device according to the present invention comprises electronic means to measure the intensity of the prompt gammas in synchrony with the RF frequency of the particle accelerator.

The electronic means for measuring the prompt gammas in synchrony with the RF frequency of the particle accelerator can be, for example, conventional electronics used in nuclear physics.

For example timing NIM modules (Nuclear Instrumentation Modules, NIM) can be used.

The basic NIM module that can be used for timing analysis is the TAC module (time to analogical convertor) which produces an output pulse with amplitude directly proportional to the time between a start input signal and a stop input signal.

This TAC can be used to measure the time between the start of an RF pulse signal (start input) and the moment a radiation event is detected in the gamma camera (stop input).

Depending on the geometry of the facility where the prompt gammas are measured in a treatment room, the RF signal can be delayed to take into account the time needed for the particles of the particle beam to travel from the accelerator to the treatment room. This delay can also be performed with a standard NIM delay module.

The NIM electronics are linked with a data acquisition system and user interface. The basic data that are acquired for each radiation event in the gamma camera are its energy deposited and the characteristic time measured with the TAC (corresponding to a TOF measurement).

All acquired radiation events can then for example be plotted as function of the time determined with the TAC, this is the time of flight spectrum.

As discussed above due to the difference in time of flight (TOF) between prompt gammas and neutrons a discrimination between prompt gammas and neutrons can be made. By setting an additional window on the measured energy of the radiation events, the discrimination between neutrons and prompt gammas can be further increased.

Alternatively, a non-intercepting particle beam detector which allows to detect the presence of a particle beam in the beam line can be used as a start signal for performing a TOF measurement as discussed above.

Embodiment 1

In one preferred embodiment an Anger camera (10) is used to detect the prompt gammas emitted in a direction essentially at 90° with respect to the beam direction.

The camera (10) is installed such that its optical axis (9) is perpendicular to the beam direction, in order to detect prompt gammas emitted from the object at 90°.

The same principle can be used by putting the camera in a different geometry with respect to the beam direction and measuring prompt gammas at different angles.

The Anger camera (10) is equipped with appropriate shielding against neutrons, X-ray and unwanted gamma-rays.

Figure 4:
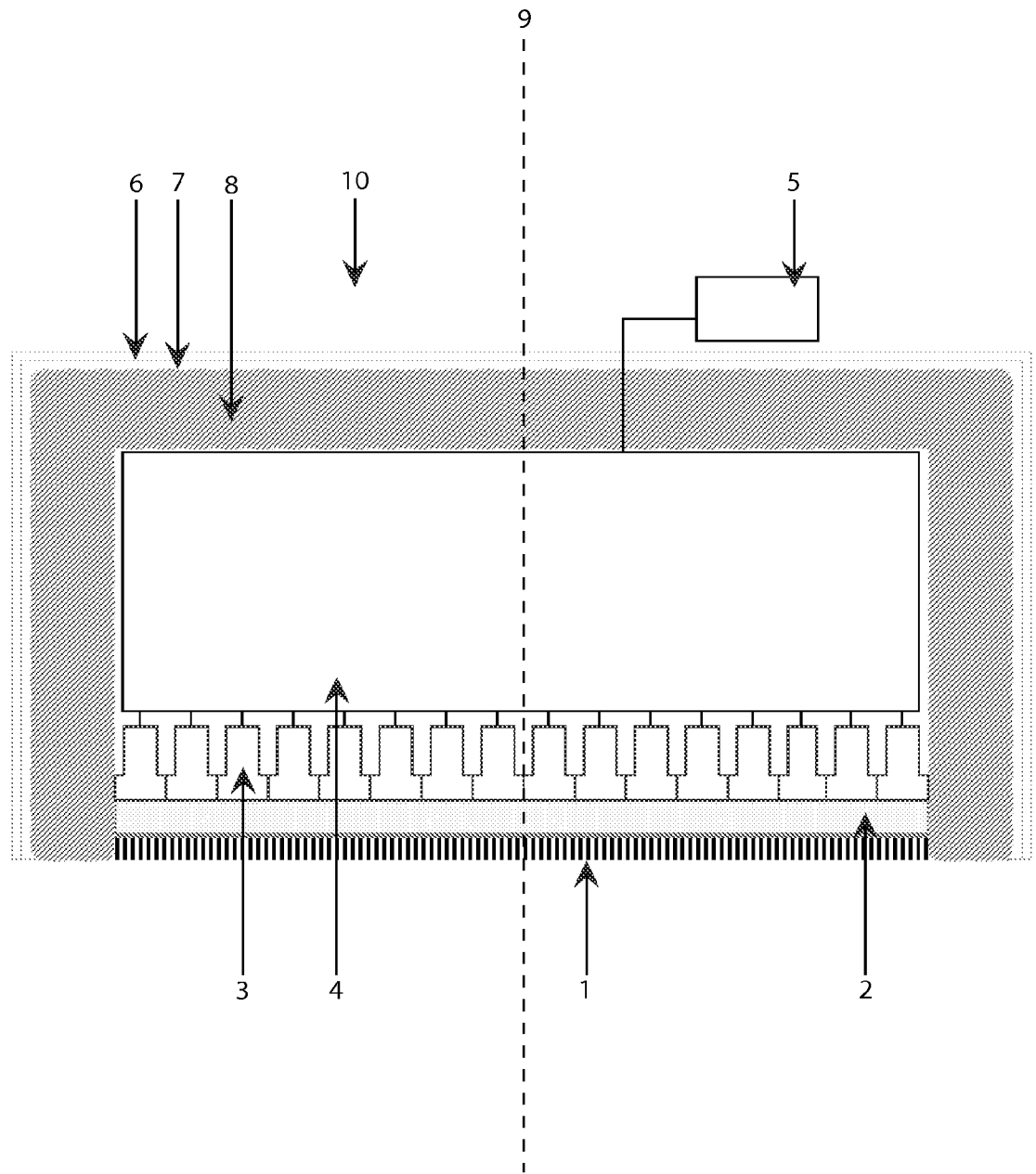
FIG. 4 presents a gamma camera arranged to detect prompt gammas according to the first embodiment of the invention.

As depicted in FIG. 4 the camera (10) comprises a plurality of collimators (1) that are made of high atomic number material such as Pb or W, on top of which at least one scintillating crystal (2) is laid.

The at least one scintillating crystal is optically coupled to at least one photomultiplier tube (3), each of them being connected to appropriate readout electronics (4).

Therefore, the said camera comprises means that enable counting of prompt gammas emitted by the irradiated body or by the irradiated object.

Preferably, the photomultiplier tubes (3) are forming a linear array.

More preferably, the photomultiplier tubes (3) are forming a two dimensional array.

The appropriate readout electronics (4) are connected to computing means such as a PC (5).

The collimator (1) comprises a set of thick sheets of high atomic material—usually 2.5 cm to 8 cm thick—that are all parallel to each other and perpendicular to the plane defined by the scintillation crystal(s). In this way, the camera comprises a plurality of collimators and can thus detect prompt gammas emitted from a whole body or object without performing any movement relatively to this body or object.

The at least one scintillating crystal (2) is made of scintillation material such as sodium iodine with thallium doping.

Each scintillating crystal is light-sealed avoiding signal cross-contamination between adjacent crystals.

The shielding of neutrons is composed of two layers (6,7). The outer layer (6) is made of material that reduces the energy of fast neutrons, such as paraffin or high density polyethylene, whereas the inner layer (7) is made of material capturing the low energy neutrons by the (n,γ) neutron capture reaction, such as $B_4C$ powder, Cd layer or a plastic doped with Li or B.

A third layer (8), e.g. Pb or W, allows to shield against unwanted photons such as photons generated by inelastic scattering reactions and photons generated by the said (n,γ) neutron capture reaction.

The appropriate readout electronics (4) connected to computing means, such as a PC (5), enables to build a distribution of prompt gammas. This distribution is representative of the relative dose distribution in the irradiated object or body.

The distribution is either a one dimensional (1-D) or a two dimensional (2-D) representation of the dose distribution in the object.

Preferably, a second camera identical to the first one is used to detect prompt gammas and to build a second distribution of prompt gammas.

The combination of these distributions enables to build a three dimensional (3-D) distribution of prompt gammas thanks to dedicated software running on computing means (5).

Preferably, the 2-D and 3_D distribution are represented using 2-D or 3-D maps generated by imaging software running on computing means (5).

Embodiment 2

In another preferred embodiment a pinhole camera is used to detect the prompt gammas emitted from the irradiated body or object.

The camera is installed such that is optical axis (30) is perpendicular to the beam direction 50 in order to detect prompt gammas emitted from the object.

The pinhole gamma camera is equipped with shielding against neutrons, X-ray and unwanted gamma-rays.

Figure 5:
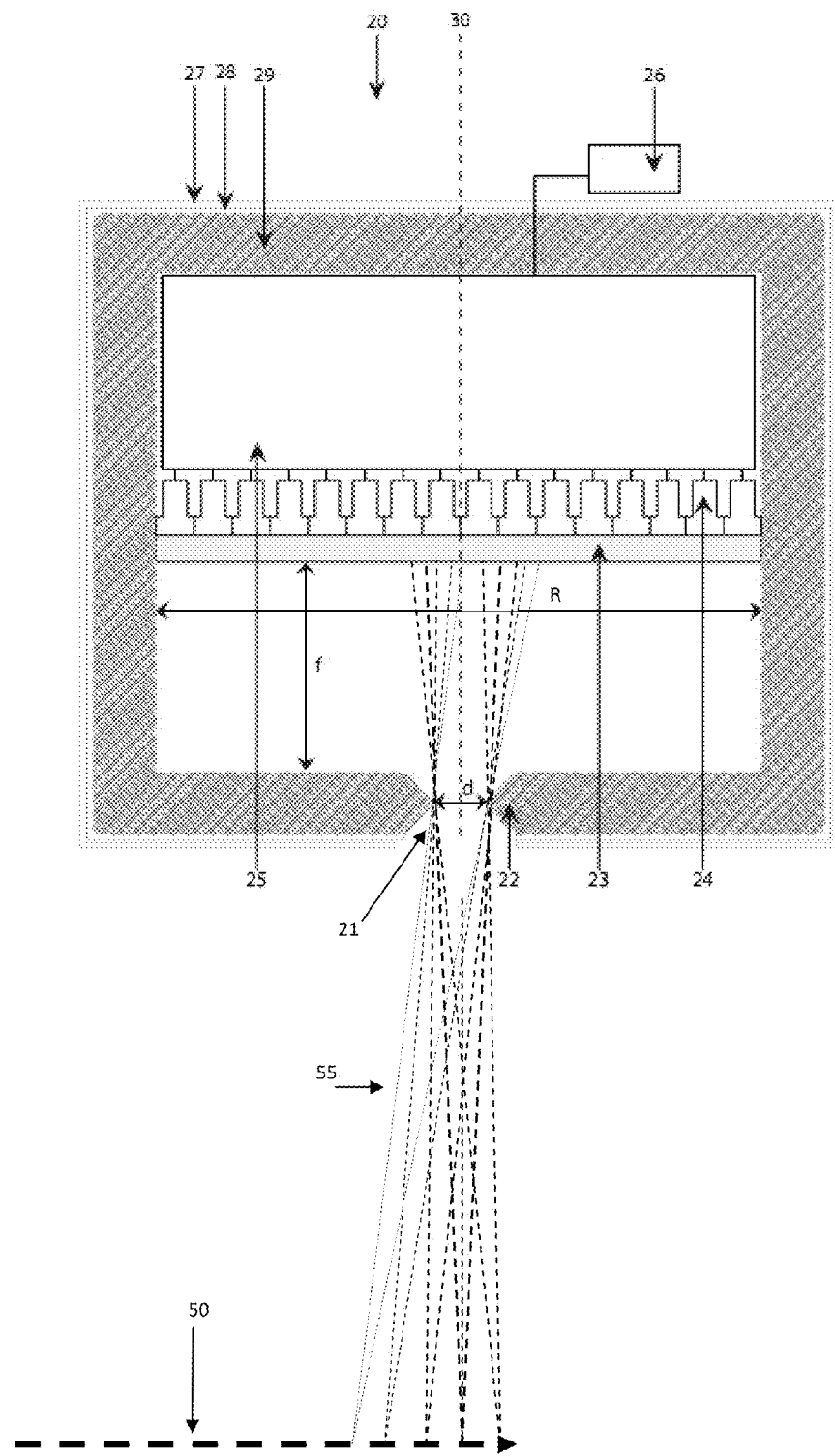
FIG. 5 presents a pin-hole camera arranged to detect prompt gammas according to the second embodiment of the invention.

As depicted in FIG. 5 the pinhole camera (20) is equipped with a pinhole collimator (21) made in a high atomic number material such as Pb or W.

An advantage of using a pin-hole camera when compared with an Anger camera is that a pin-hole camera can be better shielded for background irradiation.

A problem with the Anger camera is the fact that to obtain a high resolution when measuring the distribution of prompt gammas, the distance between the collimators is small (few mm, e.g. 2 or 3 mm) and hence the effective shielding is reduced.

Preferably, the section following any plane comprising the optical axis (30) of the pinhole has a conical shape (22). The conical shape enables to detect prompt gammas that are not emitted from 90° of the beam direction.

Therefore, the camera can detect prompt gammas 55 emitted from a whole body or an object without performing any movement relatively to this body or object.

Preferably, the camera is motionless during the irradiation of the object or the body.

Eventually, the camera is able to move during the irradiation of the object or the body.

Preferably, the inner diameter d of the pinhole is strictly superior to the value of the wavelength of the most energetic emitted prompt gammas. Below this value diffraction of photons occurs.

The pinhole camera comprises at least one scintillating crystal (23) optically coupled to at least one photomultiplier tube (24), each of them being connected to a appropriate readout electronics (25).

Therefore, the said camera comprises means that enable counting of prompt gamma emitted by the irradiated body or by the irradiated object.

Preferably, the photomultiplier tubes (24) are forming a linear array.

More preferably, the photomultiplier tubes (24) are forming a two dimensional array.

The at least one scintillating crystal (23) is made of scintillation material such as sodium iodine with thalium doping.

Preferably, each scintillating crystal is light-sealed avoiding signal cross-contamination between adjacent crystals.

Preferably, the shielding of neutrons is composed of two layers (27,28). The outer layer (27) is made of material that reduces the energy of fast neutrons such as paraffin or high density polyethylene, whereas the inner layer (28) is made of material capturing the neutrons by the (n,γ) reaction, such as $B_4C$ powder, Cd layer or a plastic compound doped with Li or B.

Preferably, a third layer (29), e.g. Pb or W, allows to shield against unwanted photons such as photons generated by inelastic scattering reactions, photon generated by the said (n,γ) neutron capture reaction (cf. infra) and prompt gamma produced at large angle.

We mean by prompt gamma produced at large angle prompt gamma that go through the pinhole with an angle—relatively to the optical axis (30)—which exceed the value given by the formula:

$$\beta = arctg(R/(2f))$$

Where f is the focal length, i.e. the distance between the pinhole and the surface of the scintillation material, and where R is the longitudinal length of the scintillation material.

The appropriate readout electronics (25) linked to computing means (26), such as PC, enables to build a two dimensional (2D) distribution of prompt gammas. The 2D distribution is representative of the relative dose distribution in the irradiated object or body.

Preferably, the pinhole camera is composed of a set of pinhole cameras (minimum two) installed around the beam direction.

The appropriate readout electronics (4) connected to computing means, such as a PC (5), enables to build a distribution of prompt gammas. This distribution is representative of the relative dose distribution in the irradiated object or body.

The distribution is either a one dimensional (1-D) or a two dimensional (2-D) representation of the dose distribution in the object.

Preferably, a second camera identical to the first one is used to detect prompt gammas and to build a second distribution of prompt gammas.

Alternatively, a second camera different of the first one is used to detect prompt gammas and to build a second distribution of prompt gammas.

Advantageously, the optical axis of the two cameras are orthogonal.

Each pinhole camera detects prompt gammas and builds a 2D distribution of prompt gammas.

The combination of these 2D distributions enables to build a three dimensional (3-D) distribution of prompt gamma thanks to dedicated software.

The combination of these distributions enables to build a three dimensional (3-D) distribution of prompt gammas thanks to dedicated software running on computing means (5).

Preferably, the 2-D and 3_D distribution are represented using 2-D or 3-D maps generated by imaging software running on computing means (5).

The device according to the invention can be verified and/or calibrated by performing a comparison measurement in a phantom (e.g. water phantom).

The deduced range based on the prompt gamma detection can be compared with the range obtained by using a dedicated range measuring device (e.g. ionization chamber, diode, . . . ).

Another aspect of the present invention relates to a method for verifying and/or calibrating the device of the present invention comprises the steps of:
 irradiating a phantom with a charged hadron beam;
 detecting the emitted prompt gammas during irradiation;
 deducing from the detected prompt gammas the range or penetration depth of the said charged hadron beam;
 measuring the range of the charged hadron beam in the phantom with a dedicated range measuring device;
 comparing the deduced range based on the prompt gamma detection with the range measured with the said dedicated range measuring device.

The device according to the present invention can further be used in a method comprising the steps of:
 irradiating a patient with a charged hadron beam;
 detecting the emitted prompt gammas during patient irradiation, i.e. while the said hadron beam is penetrating the patient's body;
 deducing from the detected prompt gammas the range or penetration depth of the said charged hadron beam.

In addition, the device according to the invention can also be used in a method comprising the steps of:
 detecting prompt gammas emitted during patient irradiation with a hadron beam;
 deducing from the detected prompt gammas the dose distribution in the patient resulting from said irradiation.

In addition, the device according to the invention can also be used in a method comprising the steps of:
 detecting prompt gammas emitted during patient irradiation with a hadron beam;
 calculating the radiation dose given to the patient based on the detected prompt gammas.

The invention claimed is:

1. A device for charged hadron therapy verification by detecting and/or quantifying prompt gammas produced when irradiating an object or a body with a charged hadron beam, said device comprising a gamma-ray pin-hole camera arranged to acquire a number of said prompt gammas emitted while the charged hadron beam is penetrating the object or body, wherein the pinhole camera comprises at least one scintillating crystal optically coupled to a plurality of photomultiplier tubes which form a linear or two-dimensional array, and wherein said pin-hole camera comprises a pinhole collimator made of a high atomic number material and having a conically shaped hole enabling detection of prompt gammas that are not emitted from 90° of the beam direction.

2. The device according to claim 1, wherein said gamma-ray pinhole camera further comprises additional shielding means to avoid detection of unwanted particles.

3. The device according to claim 1, wherein said gamma-ray pin-hole camera comprises electronic means for data acquisition.

4. The device according to claim 3, further comprising computing means connected to said electronic means to enable determination from the counted said prompt gammas, of a measured penetration depth or range of said charged hadron beam in said object or body.

5. The device according to claim 4, wherein said computing means enables comparison of the measured penetration depth with the theoretical or planned penetration depth.

6. The device according to claim 4, wherein said computing means connected to said electronic means enables building an image representing a relative dose deposition.

7. The device according to claim 6, wherein said image is a two-dimensional or three-dimensional representation of the relative dose deposition.

8. The device according to claim 1, wherein an optical axis of the camera is perpendicular to the direction of the beam.

9. The device according to claim 1, wherein an inner diameter of the pinhole is strictly superior to a value of a wavelength of emitted prompt gammas which are most energetic.

10. The device according to claim 1 further comprising electronic means to acquire the number of said prompt gammas in synchrony with a time structure of said charged hadron beam.

11. A method for charged hadron therapy verification by detecting prompt gammas obtained by irradiating a phantom with a particle beam comprising the steps of:
 positioning a prompt gamma detector in a fixed position relatively to the phantom;
 irradiating the phantom with a charged hadron beam;
 detecting emitted prompt gammas during irradiation;
 deducing from the detected prompt gammas a range or penetration depth of the charged hadron beam;
 measuring the range of the charged hadron beam in the phantom with a dedicated range measuring device;
 comparing the deduced range based on the prompt gamma detection with the range measured with the dedicated range measuring device,
 wherein the prompt gamma detector is a gamma-ray pinhole camera comprising at least one scintillating crystal optically coupled to a plurality of photomultiplier tubes which form a linear or two-dimensional array, and wherein said pin-hole camera comprises a pinhole collimator made of a high atomic number material and having a conically shaped hole, enabling to detect prompt gammas that are not emitted from 90° of the beam direction.

12. The method according to claim 11 further comprising the step of calculating a radiation dose given to a phantom based on the detected prompt gammas.

13. A device for charged hadron therapy verification by detecting and/or quantifying prompt gammas produced when irradiating an object or a body with a charged hadron beam, said device comprising a gamma-ray pin-hole camera arranged to acquire a number of said prompt gammas emitted while the charged hadron beam is penetrating the object or body, and wherein said pin-hole camera comprises a pinhole collimator made in a high atomic number material and having a conically shaped hole which enables detection of prompt gammas that are not emitted from 90° of the beam direction.

14. A device used in combination with charged hadron therapy, which therapy uses a charged hadron beam, the device configured and arranged to detect prompt gammas produced when irradiating and penetrating an object with the charged hadron beam, the device comprising:
- a pinhole camera arranged and configured in the device to detect the prompt gammas emitted when the charged hadron beam penetrates the object, the pinhole camera including:
- a shielding housing; and
- at least one scintillating crystal in the shielding housing;
- at least one photomultiplier tube optically coupled to the at least one scintillating crystal in the shielding housing,
- the shielding housing having an access hole through the shielding housing, the access hole having side walls which define a hole cross section which angles inward as the hole extends from outside to inside the housing, the pinhole camera configured and arranged in the device such that the pinhole camera is effective to detect prompt gammas that are not emitted 90° from the hadron beam direction.

15. The device according to claim 14, wherein the shielding housing is effective to avoid detection of unwanted particles.

16. The device according to claim 15, wherein the device further comprises an electronic device which is effective for data acquisition.

17. The device according to claim 16, further comprising a computer connected to the electronic device, the computer in combination with the electronic device effective for determining from counted prompt gammas a measured penetration depth or range of the charged hadron beam in the object or body.

18. The device according to claim 17, wherein the computer is effective to compare a measured penetration depth with a theoretical or planned penetration depth.

19. The device according to claim 17, wherein the computer connected to the electronic device is effective to build an image representing a relative dose deposition.

20. The device according to claim 19, wherein the image is a two-dimensional or three-dimensional representation of the relative dose deposition.

21. The device according to claim 14, wherein an optical axis of the camera is perpendicular to the direction of the beam.

22. The device according to claim 14, wherein an inner diameter of the pinhole is strictly superior to a value of a wavelength of emitted prompt gammas which are most energetic.

23. The device according to claim 14 further comprising an electronic device which is effective to acquire a number of prompt gammas in synchrony with a time structure of the charged hadron beam.

24. A device for use in charged hadron therapy verification by detecting and/or quantifying prompt gammas produced when irradiating and penetrating an object or a body with a charged hadron beam, the device comprising:
- a gamma-ray pin-hole camera arranged to acquire a number of the prompt gammas emitted while the charged hadron beam is penetrating the object or body; and
- a shielding housing, the shielding housing having an access hole through the shielding housing, the access hole having side walls which define a hole cross section which angles inward as the hole extends from outside to inside the housing, the pinhole camera configured and arranged in the device such that the pinhole camera is effective to detect prompt gammas that are not emitted 90° from the hadron beam direction.

25. The device according to claim 24, wherein the device further comprises an electronic device which is effective for data acquisition.

26. The device according to claim 25, further comprising a computer connected to the electronic device, the computer in combination with the electronic device effective for determining from counted prompt gammas a measured penetration depth or range of the charged hadron beam in the object or body.

27. The device according to claim 26, wherein the computer is effective to compare a measured penetration depth with a theoretical or planned penetration depth.

28. The device according to claim 27, wherein the computer connected to the electronic device is effective to build an image representing a relative dose deposition.

29. The device according to claim 28, wherein the image is a two-dimensional or three-dimensional representation of the relative dose deposition.

30. The device according to claim 24, wherein an optical axis of the camera is perpendicular to the direction of the beam.

31. The device according to claim 24, wherein an inner diameter of the pinhole is strictly superior to a value of a wavelength of emitted prompt gammas which are most energetic.

32. The device according to claim 24 further comprising an electronic device which is effective to acquire a number of prompt gammas in synchrony with a time structure of the charged hadron beam.

* * * * *